(12) United States Patent
Park et al.

(10) Patent No.: US 10,912,670 B2
(45) Date of Patent: Feb. 9, 2021

(54) ORAL APPLIANCE AND METHOD FOR MANUFACTURING THE SAME

(71) Applicants: Young Hyon Park, Incheon-si (KR); Pasamedi Co., Ltd., Incheon-si (KR)

(72) Inventors: Young Hyon Park, Incheon-si (KR); Hyun Jin Choi, Incheon-si (KR); Jun Young Park, Incheon-si (KR); Jun Won Park, Incheon-si (KR)

( * ) Notice: Subject to any disclaimer, the term of this patent is extended or adjusted under 35 U.S.C. 154(b) by 443 days.

(21) Appl. No.: 15/841,351

(22) Filed: Dec. 14, 2017

(65) Prior Publication Data
US 2019/0175387 A1 Jun. 13, 2019

(30) Foreign Application Priority Data
Dec. 7, 2017 (KR) .......................... 10-2017-0167184

(51) Int. Cl.
*A61F 5/56* (2006.01)
*B33Y 80/00* (2015.01)
*B33Y 50/02* (2015.01)
*B33Y 10/00* (2015.01)

(52) U.S. Cl.
CPC .............. *A61F 5/566* (2013.01); *B33Y 10/00* (2014.12); *B33Y 50/02* (2014.12); *B33Y 80/00* (2014.12)

(58) Field of Classification Search
CPC ....................................................... A61F 5/566
See application file for complete search history.

(56) References Cited

FOREIGN PATENT DOCUMENTS

| KR | 10-1074536 | 10/2011 |
|---|---|---|
| KR | 10-1154618 | 6/2012 |
| KR | 10-1301525 | 9/2013 |
| KR | 10-1463021 | 11/2014 |
| KR | 10-1706648 | 2/2017 |

OTHER PUBLICATIONS

English translation of 10-1074536.
English translation of 10-1154618.
English translation of 10-1706648.
English translation of 10-1301525.
English translation of 10-1463021.

*Primary Examiner* — James Sanders
(74) *Attorney, Agent, or Firm* — Antonio Ha & U.S. Patent, LLC

(57) ABSTRACT

The present invention relates to an oral appliance, and more specifically, to an oral appliance enabling comfortable oral motor exercises while being effectively fastened to teeth by applying differing degrees of fastening to teeth to its incisor part and molar part. In the oral appliance and method for manufacturing the same according to the present invention, different degrees of fastening are applied to the incisor part and the molar part, thereby minimizing the user's inconvenience that arises when the user moves mouth while keeping the oral appliance stably fastened to the teeth.

10 Claims, 9 Drawing Sheets

ORAL APPLIANCE AND METHOD FOR MANUFACTURING THE SAME

CROSS-REFERENCE TO RELATED APPLICATIONS

This patent application claims priority under 35 U.S.C. § 119 to Korean Patent Application No. 10-2017-0167184, filed on Dec. 7, 2017, in the Korean Intellectual Property Office, the disclosure of which is incorporated by reference herein in its entirety.

TECHNICAL FIELD

The present invention relates to an oral appliance, and more specifically, to an oral appliance enabling comfortable oral motor exercises while being effectively fastened to teeth by applying differing degrees of fastening to teeth to its incisor part and molar part.

DISCUSSION OF RELATED ART

When a human being falls asleep, his body muscles relax. In particular, the relaxation of the tongue, uvula, soft palate, or tonsils may pressurize and narrow the airway. In this case, the air inhaled flows fast as passing through the narrowed airway, vibrating the peripheral soft tissues with the result of snoring. Severe snoring may block the airway during sleep, leading to obstructive sleeping apnea (OSA) which pauses breathing. When either apnea, characterized by complete cessation of airflow for at least 10 seconds at the nose or mouth, or hypopnea, occurs five times or more per hour, it is diagnosed of OSA which may cause hypoxemia, an increase in carbon dioxide in blood, stroke, heart rate anomaly, or sudden death. OSA has also been known as deeply related to diabetes. Moreover, snoring and OSA disturb deep sleep, inducing persistent and chronic daytime fatigue that results in poor performance in the workplace.

To treat snoring and OSA, there have been ongoing research efforts—they are largely classified into surgical treatment and non-surgical treatment. Surgical treatment involves expanding the narrowed airway by surgery. This method, however, suffers from high risk, a likelihood to develop a complication, and frequent recurrence. This way also has the shortcomings of surgery that is irrrecoverable once done. Non-surgery treatment encompasses chemical methods, e.g., via use of medications and physical methods, such as those using oral appliances, e.g., mandibular advancement devices (MADs) or continuous positive airway pressure (CPAP).

ACPAP is a sort of ventilator that forces air to flow through the airway to expand the obstructed airway. Despite its superior effects, however, ACPAP is subject to various disadvantages, such as high purchase cost, displeasure in putting on the user's face, and inconvenience in carrying. The MAD which is worn in the user's mouth moves the user's lower jaw forward, allowing the tongue, which is attached to the mandibular bone, to be pulled forward so that the peripheral soft tissues sagged are spread to secure the airway. As the user secures the airway by wearing the MAD, air inhaled flows naturally to the airway while preventing the peripheral soft tissues from vibrating. Thus, snoring reduces or vanishes. This smoothly increases the air flow into the airway to the normal amount, enabling treatment of OSA.

Conventional techniques related to oral appliances are disclosed in Korean Patent No. 10-1074536, titled "Mandibular Advancement Device," Korean Patent No. 10-1154618, titled "Mandible Induced Jaw Function Device for Orthodontics," and Korean Patent No. 10-1706648, titled "Orthodontic Instrument for Occlusal Position." Korean Patent No. 10-1074536 discloses a structure able to adjust the position of a lower teeth fastening part using, e.g., a screw. Korean Patent No. 10-1154618 discloses a structure in which a micro actuator is mounted in the device to restrict the back-and-forth movement of a block attached to the lower jaw along a straight line. However, mounting an electrical or mechanical moving device in a human mouth may damage the human body due to a short circuit or the mechanical parts of the device. Korean Patent No. 10-1706648 discloses an orthodontic instrument for occlusal position in which an upper teeth fastening part and a lower teeth fastening part are connected together via twin blocks, e.g., elastic bodies, to separate the upper jaw from the lower jaw. However, the twin-block structure for separating upper jaw and lower jaw require a separate connecting device because an independent upper jaw device and lower jaw device should be connected together, resulting in the oral appliance being bulky. Further, the need for a precise connection causes it difficult to manufacture the device and maintain the connecting device. Further, since the upper jaw and the lower jaw are overall connected via the connecting device, no precise occlusion is obtained when the upper jaw device and the lower jaw device, which are separated from each other, come in contact with each other, causing malocclusion.

Such oral appliance moves the lower jaw forward, allowing the tongue to naturally be pulled forward and thereby riding the airway of pressure on it by the tongue. However, where the user unconsciously opens his mouth during sleep to breathe in oxygen which is deplete, the lower jaw which has been forced to advance may be moved back to the original position, which may get rid of the effect of preventing snoring. After the oral appliance is worn in the user's mouth, the user may have difficulty in speaking, opening mouth, or yawing. Further, the temporomandibular joint disk is overloaded, causing pain in not only temporalis but also sternocleidomastoid, trapezius, muscles of mastication, or other adjacent muscular system, and temporomandibular disorder. Such side effects may arise not just in the twin block structure which separates the upper jaw from the lower jaw but also in the monoblock structure in which the upper and lower teeth are received in a single body.

To address such issues, the inventors have received patents relating to oral appliances fastened to the upper jaw via friction from the teeth while securing flexibility, which are disclosed in Korean Patent No. 10-1301525, titled "Lower Jaw Advancement Snoring Preventing Oral Appliance Intended for Both Upper Jaw and Lower Jaw Which Permits Slight Movement of Temporomandibular Joint" and Korean Patent No. 10-1463021, titled "Oral Appliance." In order to secure the mobility of lower jaw, the molars need to be tightly fastened to the oral appliance, but the anterior teeth are required to secure as much mobility for up-and-down movement as possible to minimize the user's inconvenience or efficiently preventing snoring.

PRIOR TECHNICAL DOCUMENTS

Patent Documents

Korean Patent No. 10-1074536 (issued on Oct. 17, 2011)
Korean Patent No. 10-1154618 (issued on Jun. 8, 2012)
Korean Patent No. 10-1706648 (issued on Feb. 14, 2017)
Korean Patent No. 10-1301525 (issued on Sep. 2, 2013)
Korean Patent No. 10-1463021 (issued on Nov. 18, 2014)

SUMMARY

The present invention addresses the above issues, aiming to provide an oral appliance allowing for convenient oral motor exercises while effectively keeping the oral appliance fastened to the teeth by applying different degrees of fastening to the incisor part and the molar part and a method for manufacturing the same.

To achieve the above objects, according to the present invention, a method for manufacturing an oral appliance may comprise replicating a teeth impression of teeth and peripheral tissues, forming a blocking on the teeth replica, wherein different blocking margins are applied to an incisor part and a molar part, designing the oral appliance using the blocking-formed teeth replica, and manufacturing the designed oral appliance.

Replicating the teeth impression of the teeth and the peripheral tissues may include replicating an appearance of the teeth and the peripheral tissues using a medical material, creating a teeth cast by hardening plaster on the replicated appearance of the teeth and the peripheral tissues, and creating the teeth replica using the teeth cast.

Replicating the teeth impression of the teeth and the peripheral tissues may include replicating an appearance of the teeth and the peripheral tissues using a medical material, creating a teeth cast by hardening plaster on the replicated appearance, obtaining three-dimensional (3D) data by scanning or capturing the teeth cast in 3D, and creating the teeth replica using the 3D data.

Replicating the teeth impression of the teeth and the peripheral tissues may include obtaining 3D data for a teeth structure by scanning or capturing a user's mouth in 3D and creating the teeth replica using the 3D data.

Forming the blocking may include, when the blocking is formed on the incisor part, setting a thickness of the blocking using, as a blocking margin, a space between a tangential line and a vertical line for an edge surface of anterior teeth and attaching the blocking to a surface of the incisor part depending on the blocking margin.

The blocking margin may be a distance of 2.5 mm or less away from the edge surface of the anterior teeth.

Forming the blocking may include, when the blocking is formed on the molar part, setting a thickness of the blocking using, as a blocking margin, a maximum width of a molar and attaching the blocking to a surface of the molar part depending on the blocking margin.

The blocking margin may be a distance of 2 mm or less away from a side surface of the molar.

Designing the oral appliance may include obtaining the 3D data by scanning or capturing the blocking-formed teeth replica in 3D.

The oral appliance may be manufactured by attaching or applying a medical material onto an outside of the blocking-formed teeth replica.

The oral appliance may be manufactured by at least one or more of methods using a 3D printer, a CAD, and a cam depending on the designed data.

According to the present invention, an oral appliance may comprise a body having a shape corresponding to dentition, an upper groove formed in an upper part of the body to fit over teeth of an upper jaw, a lower groove formed in a lower part of the body to fit over teeth of a lower jaw and to allow the lower jaw to move forward at a predetermined distance, and a guide part formed to extend from the body to face a side surface of the teeth of the upper jaw or the lower jaw, wherein an incisor part corresponding to anterior teeth in the upper groove or the lower groove may have an inner wall to be spaced a predetermined distance apart from a space between a tangential line and a vertical line for an edge surface of the anterior teeth, and a molar part corresponding to at least one or more molars in the upper groove or the lower groove may have an inner wall to be spaced apart at a predetermined distance with respect to a maximum width of the molars.

The body may be formed of a material safe to a human body, the material including a medical resin or silicone.

The incisor part may be spaced 2.5 mm or less apart from an edge surface of the anterior teeth.

The molar part may be spaced 2 mm or less apart from a side surface of the molars.

In the oral appliance and method for manufacturing the same according to the present invention, different degrees of fastening are applied to the incisor part and the molar part, thereby minimizing the user's inconvenience that arises when the user moves mouth while keeping the oral appliance stably fastened to the teeth.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF EXEMPLARY EMBODIMENTS

Figure 1:
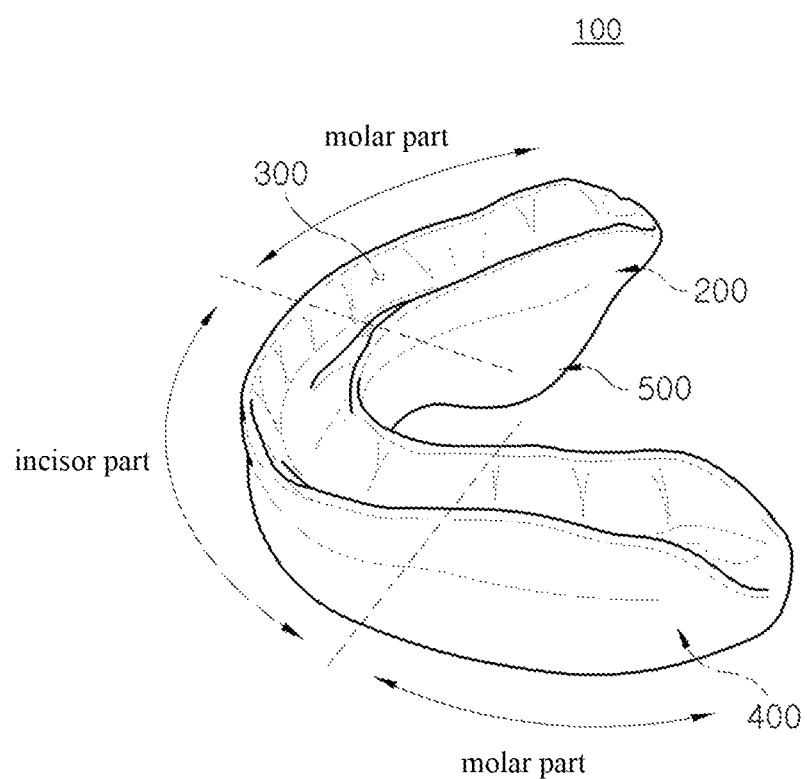
FIG. 1 is a perspective view illustrating an oral appliance according to an embodiment of the present invention.

The terminologies used herein are only for describing particular embodiments and are not intended to limit the present invention. Singular forms as used herein include plural forms unless stated otherwise. The term "comprise" as used herein is used to embody a particular characteristic, region, integer, step, operation, element, and/or component without excluding presence or addition of other particular characteristics, regions, integers, steps, elements, components, and/or groups.

The terms "upper," "top," "lower," "bottom," left," and "right" as used herein refer to relative relations in positions among the elements shown in the drawings and should not be intended to limit the present invention. The terms "first," "second," "third," and "fourth" as used herein are used in the following detailed description to refer to various elements, regions, or sections, but such elements, regions, or sections should not be limited by the terms. The terms are used merely to distinguish one element, region, or section from another. Therefore, the term "first element," "first region," or "first section" as used herein should also be termed a "second element," "second region," or "second section" without departing form the scope of the present invention.

Unless defined otherwise, the technical or scientific terms as used herein have the same meaning as those commonly appreciated by one of ordinary skill in the art to which the present invention pertains. The terms defined in dictionaries commonly used may be construed to comply with those set forth herein and relevant technical documents and should not be interpreted overly ideally or formally unless defined otherwise.

Hereinafter, preferred embodiments of the present invention are described in detail with reference to the accompanying drawings.

According to the present invention, an oral appliance may be produced as an upper jaw fixed oral appliance which is fastened to the user's upper jaw or a lower jaw fixed oral appliance which is fastened to the user's lower jaw. Where an upper jaw fixed oral appliance and a lower jaw fixed oral appliance are distinct from each other, they are separately described. However, where embodiments of the present invention are applicable to upper jaw fixed oral appliances or lower jaw fixed oral appliances, the upper jaw fixed oral appliances and the lower jaw fixed oral appliances are described with them collectively referred to as oral appliances.

FIG. 1 is a perspective view illustrating an oral appliance according to an embodiment of the present invention; Referring to FIG. 1, an oral appliance 100 of the present invention may include a body 200, an upper groove 300, a lower groove 400, and a guide part 500. The body 200 may have a shape corresponding to an upper dentition (UD) and a lower dentition (LD). In other words, the body 200 may be shaped as a horseshoe as shown. Accordingly, the upper jaw (UJ) and the upper dentition (UD) and the lower jaw (LJ) and the lower dentition (LD) may correspond to the body 200. The body 200 may be formed of a dental resin or silicone but is not limited thereto. For example, the body 200 may be formed of any substance or material which is known and does not cause problems when worn on the user's teeth. The oral appliance 100 including the body 200, according to the present invention, may be formed by any know methods, e.g., making molds for the user's teeth (UT and LT) and peripheral tissues and shaping the molds to fit the teeth or via use of a three-dimensional (3D) printer.

The upper teeth (UT) included in the upper dentition (UD) of the upper jaw (UJ) are fitted into the upper groove 300 formed in the top of the body 200, and the lower teeth (LT) included in the lower dentition (LD) of the lower jaw (LJ) are fitted into the lower groove 400 formed in the bottom of the body 200.

In this case, the oral appliance 100 may be implemented as an upper jaw fixed oral appliance which is fastened to the user's upper jaw (UJ) or a lower jaw fixed oral appliance which is fastened to the user's lower jaw (LJ). In the upper jaw fixed oral appliance, a molar part corresponding to the molars of the upper teeth (UT) of the upper jaw (UJ) is fastened in the upper groove 300 when the upper teeth (UT) of the upper jaw (UJ) are fitted into the upper groove 300, but a molar part corresponding to the molars of the lower teeth (LT) of the lower jaw (U) is not fastened in the lower groove 400 when the lower teeth (LT) of the lower jaw (U) are fitted in the lower groove 400 and is thus relatively free to move up and down. By contrast, in the lower jaw fixed oral appliance, the molar part corresponding to the molars of the lower teeth (LT) of the lower jaw (U) is fastened in the lower groove 400 when the lower teeth (LT) of the lower jaw (U) are fitted into the lower groove 400, but the molar part corresponding to the molars of the upper teeth (UT) of the upper jaw (UJ) is not fastened in the upper groove 300 when the upper teeth (UT) of the upper jaw (UJ) are fitted in the upper groove 300 and is thus relatively free to move up and down in the upper groove 300.

The upper groove 300 may be formed in an upper part of the body 200. In the upper jaw fixed oral appliance, the upper teeth (UT) of the upper jaw (UJ) may be fitted into the upper groove 300. The upper groove 300 may have a shape overall corresponding to the upper dentition (UD) of the upper jaw (UJ), i.e., a horseshoe shape, and is preferably formed in a shape corresponding to the upper dentition (UD) of the upper jaw (UJ). In particular, the molar part of the upper groove 300, where the molars are positioned, is formed so that at least one or more molars of the upper teeth (UT) of the upper jaw (UJ) are fastened by friction. The molar part of the upper groove 300 is formed to leave no gap from the structure of the user's molars of the upper teeth (UT) of the upper jaw (UJ), allowing the upper teeth (UT) of the upper jaw (UJ) to tightly fit the molar part of the upper groove 300. In the upper jaw fixed oral appliance, the molars of the upper teeth (UT) of the upper jaw (UJ) may thus be fastened by friction, and the molars fitted into the molar part would not be escaped from the upper groove 300 of the upper jaw fixed oral appliance unless an external force larger than the frictional force is applied between the upper groove 300 and the upper teeth (UT) of the upper jaw (UJ). At this time, the lower teeth (LT) of the lower jaw (U), although able to move to the inside of the lower groove 400, would not be brought in tight contact nor fastened.

In the lower jaw fixed oral appliance, however, the lower teeth (LT) of the lower jaw (U) may be fitted and fastened in the lower groove 400. The lower groove 400 may overall have a horseshoe shape corresponding to the lower dentition (LD) of the lower jaw (U). In particular, the molar part of the lower groove 400, where the molars are positioned, is formed so that at least one or more molars of the lower teeth (LT) of the lower jaw (U) are fastened by friction. The molar part of the lower groove 400 is formed to leave no gap from the structure of the user's molars of the lower teeth (LT) of the lower jaw (U), allowing the lower teeth (LT) of the lower jaw (U) to tightly fit the molar part of the lower groove 400. In the lower jaw fixed oral appliance, the molars of the lower teeth (LT) of the lower jaw (U) may thus be fastened by friction, and the molars fitted into the molar part would not be escaped from the lower groove 400 of the lower jaw fixed oral appliance unless an external force larger than the frictional force is applied between the lower groove 400 and the lower teeth (LT) of the lower jaw (LJ). At this time, the upper teeth (UT) of the upper jaw (UJ), although able to move to the inside of the upper groove 300, would not be brought in tight contact nor fastened.

In this case, unlike the molar part brought in tight contact and fastened with the molars, an incisor part where the anterior teeth are positioned is preferably formed to be spaced a predetermined distance apart from, rather than tightly contacting, the anterior teeth to allow the anterior teeth to be relatively free to move up and down. As such, the incisor part and the molar part are configured to have different degrees of fastening to the teeth. Thus, the user's molars are fastened to the molar part while the user's anterior teeth are not fastened to the incisor part, allowing the user to wear the oral appliance and do oral motor exercises in a convenient way.

The guide part 500 may be formed to extend up or down inside or outside the body 200. The guide part 500 may guide the lower teeth (LT) of the lower jaw (LJ) and the upper teeth (UT) of the upper jaw (UJ) to easily fit into the lower groove 400 and the upper groove 300, respectively. The guide part 500 may extend up or down from the body 200. For example, the guide part 500 may extend 3 mm to 5 mm down from the body 200. However, the length in which the guide part 500 extends from the body 200 is not particularly limited and may rather be any one depending on the user's oral conditions. Further, the guide part 500 is not limited to a particular shape and may rather have any shape as long as it may function as described above.

Figure 2:
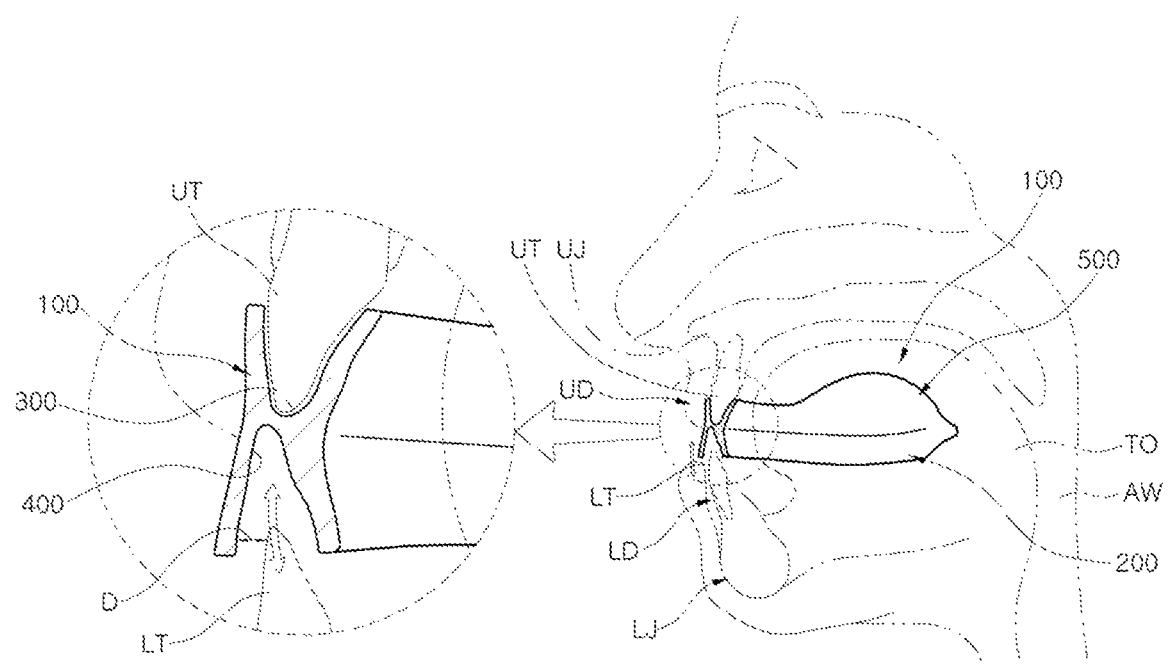
FIG. 2 is a cross-sectional view illustrating an example in which an oral appliance, according to an embodiment of the present invention, is worn, along with an expanded cross-sectional view of an incisor part.

FIG. 2 is a cross-sectional view illustrating an example in which an oral appliance, according to an embodiment of the present invention, is worn, along with an expanded cross-sectional view of an incisor part. Referring to FIG. 2, where the user wears an upper jaw fixed oral appliance of the present invention, at least one molar of the upper teeth (UT) of the upper jaw (UJ) may be fastened to an fastening part of the upper groove 300, and the lower teeth (LT) of the lower jaw (LJ) positioned in the incisor part may be fitted or escaped from the lower groove 400 while remaining at a predetermined distance D in the horizontal direction inside the lower groove 400. In this case, like the lower teeth (LT) of the lower jaw (LJ), the upper teeth (UT) of the upper jaw (UJ) may be fitted into the upper groove 300 or escaped from the upper groove 300 while remaining at a predetermined distance in the horizontal direction inside the upper groove 300. Accordingly, although the molar part may be brought in tight contact and fastened to the molars, the anterior teeth in the incisor part remain at the predetermined distance D inside the upper groove 300 or lower groove 400, allowing the anterior teeth, which move up and down in an ellipse, to stably be fitted or escaped from the oral appliance 100 without friction.

By contrast, in the lower jaw fixed oral appliance, at least one molar of the lower teeth (LT) of the lower jaw (LJ) is tightly fastened in the fastening part of the lower groove 400, where the molars are positioned, and in such state, the upper teeth (UT) of the upper jaw (UJ) may be spaced apart horizontally at the predetermined distance D inside the upper groove 300 to be fitted or escaped, or the lower teeth (LT) of the lower jaw (LJ) may be spaced apart horizontally at the predetermined distance D inside the lower groove 400 to be fitted or escaped.

Meanwhile, the guide part 500 may extend up or down from the body 200. The example shown is the case where the guide part 500 extends up. For example, the guide part 500 may extend 3 mm to 5 mm down from the body 200. However, the length in which the guide part 500 extends from the body 200 is not particularly limited and may rather be any one depending on the user's oral conditions.

In this case, the distance D at which the upper teeth (UT) of the upper jaw (UJ) are spaced apart in the horizontal direction inside the upper groove 300 or the distance D at which the lower teeth (LT) of the lower jaw (LJ) are spaced apart in the horizontal direction inside the lower groove 400 may preferably be determined in an efficient way within a range not causing inconvenience to the user's oral motor exercise given the trajectory and direction along which the upper teeth (UT) of the upper jaw (UJ) or the lower teeth (LT) of the lower jaw (LJ) move.

Figure 3:
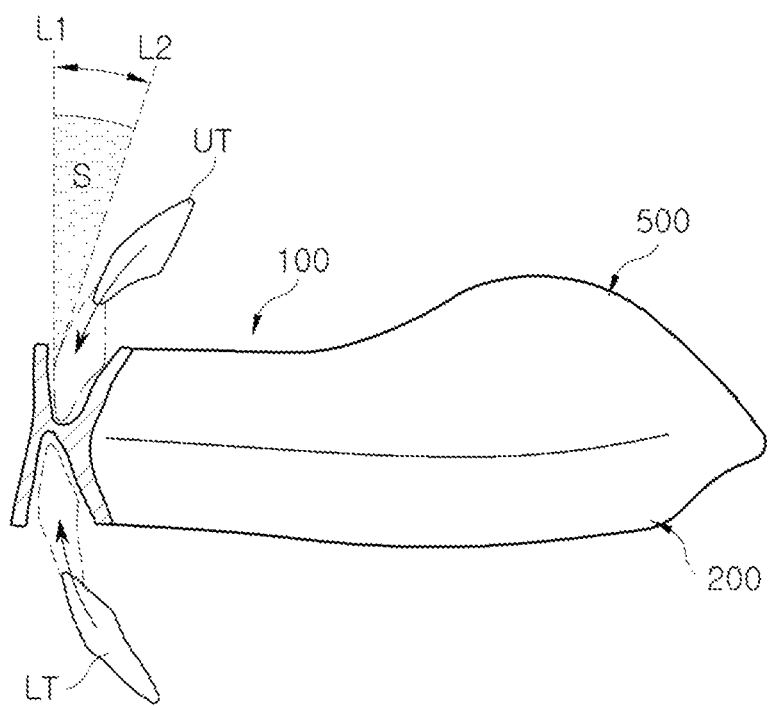
FIG. 3 is a cross-sectional view illustrating a method for determining a blocking margin in an incisor part of an oral appliance according to an embodiment of the present invention.

FIG. 3 is a cross-sectional view illustrating a method for determining a blocking margin in an incisor part of an oral appliance according to an embodiment of the present invention. In the oral appliance of the present invention, the distance D at which the upper teeth (UT) of the upper jaw (UJ) are spaced apart in the horizontal direction inside the upper groove 300 or the distance D at which the lower teeth (LT) of the lower jaw (LJ) are spaced apart in the horizontal direction inside the lower groove 400 are determined and used to apply blocking to the process of producing the oral appliance 100.

Where the oral appliance 100 of the present invention is an upper jaw fixed oral appliance, at least some of the upper molars may be tightly fastened to the upper molar part, and where the oral appliance 100 of the present invention is a lower jaw fixed oral appliance, at least some of the lower molars may be tightly fastened to the lower molar part. In contrast, the anterior teeth of the upper teeth (UT) of the upper jaw (UJ) or of the lower teeth (LT) of the lower jaw (LJ) may relatively freely move up and down without being fastened in the incisor part. At this time, the up-and-down motion of the anterior teeth may be a gentle parabolic motion rather than a motion along a vertical straight line. Accordingly, where the anterior teeth of the upper jaw (UJ) or lower jaw (LJ) are fitted into the incisor part of the oral appliance 100, it is preferable to design the structure of the upper groove 300 or lower groove 400 given the surface structure of the anterior teeth and the parabolic trajectory.

In terms of the upper teeth (UT) of the upper jaw (UJ), the state where the anterior teeth are at the foremost position may be represented as a line L1 perpendicular to the foremost edge surface of the anterior teeth when the anterior teeth are fitted in the upper groove 300 of the oral appliance 100. In other words, the foremost vertical line L1 may be considered a boundary line up to which the anterior teeth may travel. Accordingly, the internal margin of the upper groove 300 during the course of producing the oral appliance 100 of the present invention may be set based on the foremost vertical line L1 of the anterior teeth.

On the contrary, where the anterior teeth escape off the upper groove 300, the anterior teeth move back along the upper direction while making a parabola, and thus, the boundary line from which the anterior teeth escape may be set with respect to the parabola that the foremost edge surface of the anterior teeth makes. That is, when the anterior teeth draw a tangential line L2 while being fitted in the upper groove 300, the inside part behind the tangential line L2 may be a section where the anterior teeth are present. Accordingly, the space S formed by the tangential line L2 and the vertical line L1 of the foremost edge surface while the anterior teeth are fitted in the upper groove 300 of the oral appliance 100 may be set as an internal margin between the internal surface and the anterior teeth in the upper groove 300 of the oral appliance 100. Such internal margin may be used as a reference to design a blocking margin between the inner wall of the upper groove 300 and the surface of the anterior teeth in producing the oral appliance 100 of the present invention. Of course, the same reference may be applied in designing an internal margin between the lower groove 400 and the lower anterior teeth. At this time, the distance D at which the anterior teeth are spaced apart from the inner wall of the upper groove 300 or lower groove 400 is preferably set to be 2.5 mm or less.

Figure 4:
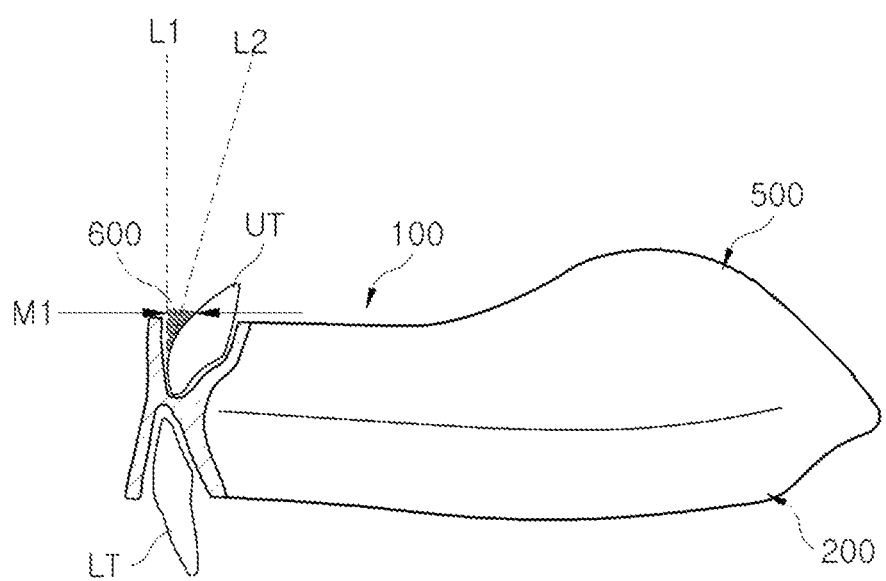
FIG. 4 is a cross-sectional view illustrating an example in which a blocking is formed in an incisor part of an oral appliance according to an embodiment of the present invention.

FIG. 4 is a cross-sectional view illustrating an example in which a blocking is formed in an incisor part of an oral appliance according to an embodiment of the present invention. Referring to FIG. 4, an oral appliance 100 of the present invention may be formed by preparing teeth molds by replicating the impressions of the user's teeth and peripheral tissues, forming a blocking 600 in the molds, and using, as a reference value, the exterior boundary of the blocking 600. In this time, the blocking margin determined above may be used as the thickness of the blocking 600 which is attached onto the outer surface of the teeth-shaped incisor part.

In other words, the thickness of the blocking 600 which is attached to the outer surface of the teeth-shaped incisor part may correspond to the space S formed by the tangential line L2 and the vertical line L1 of the foremost edge surface from the anterior teeth. In this case, the blocking 600 would have the thickness M1 from the outer surface of the anterior teeth to the space S formed by the tangential line L2 and the vertical line L1 of the foremost edge surface. While the blocking 600 is formed from the outer surface of the anterior teeth to the space S formed by the tangential line L2 and the vertical line L1 of the foremost edge surface, the value of the outer surface of the blocking 600 may be measured, and the oral appliance 100 may be designed and produced based on the value of the outer surface.

Where the user wears the oral appliance 100 so manufactured, although the upper or lower anterior teeth are fitted into the upper groove 300 or lower groove 400, the anterior teeth may be prevented from friction with the inner wall of the upper groove 300 or lower groove 400 and may be escaped from the upper groove 300 or lower groove 400 without friction with the inner wall. This allows the user to do anterior teeth exercises in a natural manner, minimizing inconvenience that may arise when wearing the oral appliance 100.

Figure 5:
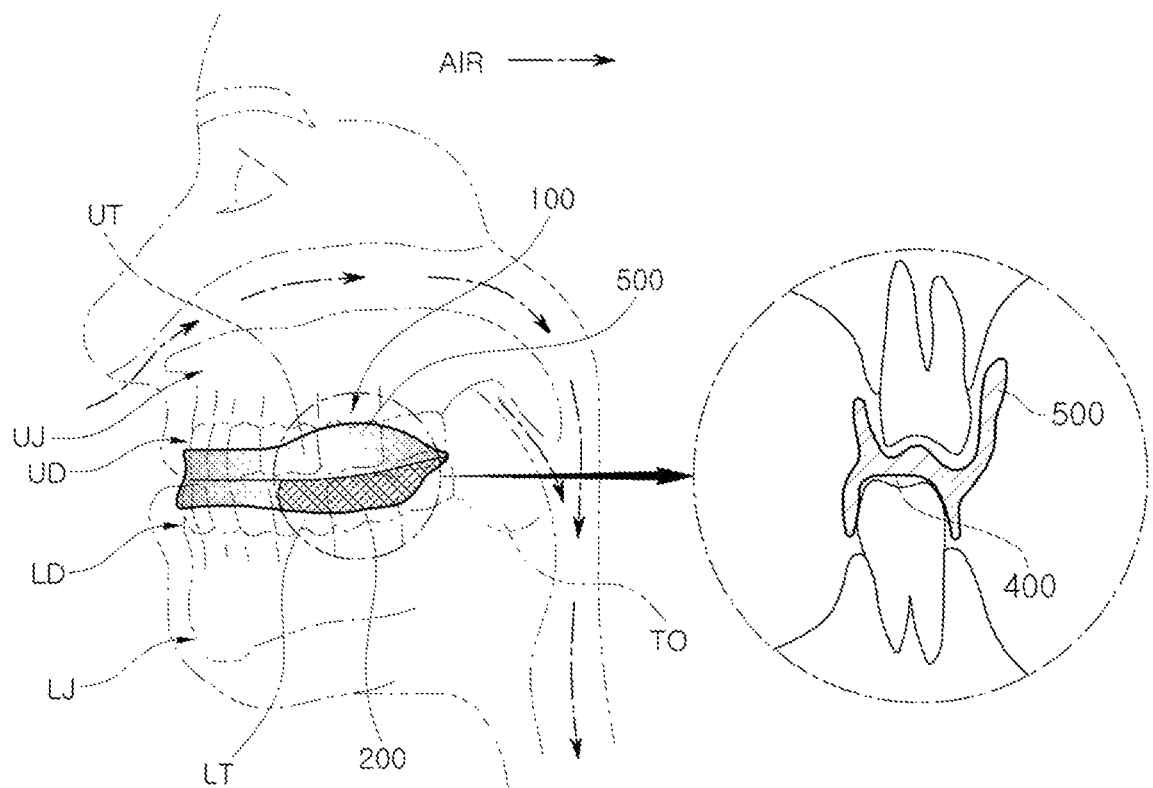
FIG. 5 is a cross-sectional view illustrating an example in which an oral appliance, according to an embodiment of the present invention, is worn, along with an expanded cross-sectional view of a molar part.

FIG. 5 is a cross-sectional view illustrating an example in which an oral appliance, according to an embodiment of the present invention, is worn, along with an expanded cross-sectional view of a molar part. Here, the oral appliance 100 may be an upper jaw fixed oral appliance or a lower jaw fixed oral appliance. It is apparent that the description, although focusing on either the upper jaw fixed oral appliance or oral appliance, may apply likewise to the other. An example is illustrated in which the molars of the lower jaw (LJ) are fitted by a frictional force in the lower groove 400 of the lower jaw fixed oral appliance. In this case, at least one of the molars of the lower teeth (LT) of the lower jaw (LJ) may be fastened by friction in the lower groove 400, which corresponds to the molars, in the oral appliance 100 of the present invention. Accordingly, the lower teeth (LT) of the lower jaw (LJ) would not escape from the lower groove 400 absent application of an external force that is larger than the fastening force which is formed by the frictional force between the molars of the lower jaw (LJ) and the fastening part of the lower groove 400. In contrast, although the upper teeth (UT) of the upper jaw (UJ) may be fitted into the upper groove 300, the upper teeth (UT) would freely move up and down without fastening to the upper groove 300.

Although the anterior teeth may move up and down along a gentle parabola in the incisor part, the molars in the molar part are tightly fastened without moving. Accordingly, a blocking margin may be determined without considering the motion of the molars, with the molar part tightly contacting within the width of the molars, unlike in the case of the anterior teeth. That is, it is preferable to determine the blocking margin of the molar part to have no blocking, or even if any, a minimum thickness, with respect to the width of the molars tightly contacted.

Figure 6:
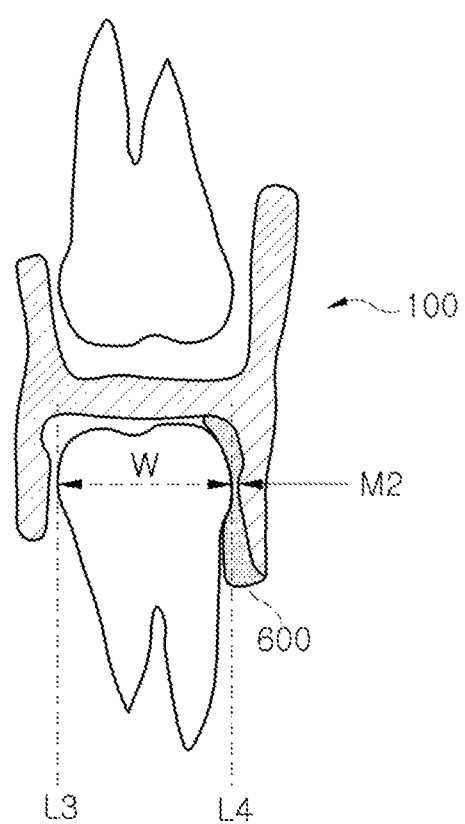
FIG. 6 is a cross-sectional view illustrating an example in which a blocking is formed in a molar part of an oral appliance according to an embodiment of the present invention.

FIG. 6 is a cross-sectional view illustrating an example in which a blocking is formed in a molar part of an oral appliance according to an embodiment of the present invention. Referring to FIG. 6, where the oral appliance 100 is a lower jaw fixed oral appliance, the molar part of the lower groove 400 is tightly fastened to at least one of the molars of the lower jaw (LJ). To that end, the inner wall of the lower groove 400 of the oral appliance 100 may be formed with respect to a maximum width along the horizontal direction from the molar tightly contacting. That is, the molar may have its maximum width W when the distance between vertical lines L3 and L4 on the left and right outermost surfaces of the molar is maximized, and the inter-inner wall distance of the molar part of the lower groove 400 of the oral appliance 100 may be determined based on the distance between the lines L3 and L4.

However, the oral appliance 100 of the present invention should be able to be escaped from the user's teeth. If the oral appliance 100 is too tightly fastened to the molars, it can be hard to escape from the teeth. Thus, a minimum distance from the maximum width W of the molar may be left. In this case, a blocking 600 is formed at a predetermined thickness M2 on the surface of the molars in the mold for the user's teeth, and the oral appliance 100 may be produced based on the surface value of the blocking 600. It is preferable to allow the thickness M2 of the blocking 600 in the molars to be 2 mm or less from the maximum width of the molar tightly contacting the lower groove 400. Although the thickness M2 of the blocking 600 is described herein for the case where the oral appliance 100 of the present invention is worn on the molars via use of a frictional force, such a case may also be possible in which the thickness M2 of the blocking 600 is 2 mm or more to reinforce the fastening force with the molars by way of an auxiliary fastening means, such as dental wires, as well as a frictional force.

Meanwhile, although the thickness M2 of the blocking 600 for the maximum width of the molar corresponds to the spacing distance for securing a fastening force between the molars and the oral appliance 100 of the present invention, since the area above or below the molar portion with the maximum width reduces in width, the thickness of the blocking 600 for such portion may be deemed a spacing distance for securing a space between the molars and the oral appliance 100 of the present invention. As such, the spacing distance for securing a space between the molars and the oral appliance 100 is preferably formed to be larger than the spacing distance which is set with respect to the maximum width of the molar, and this may be formed to be 5 mm or less.

Figure 7:
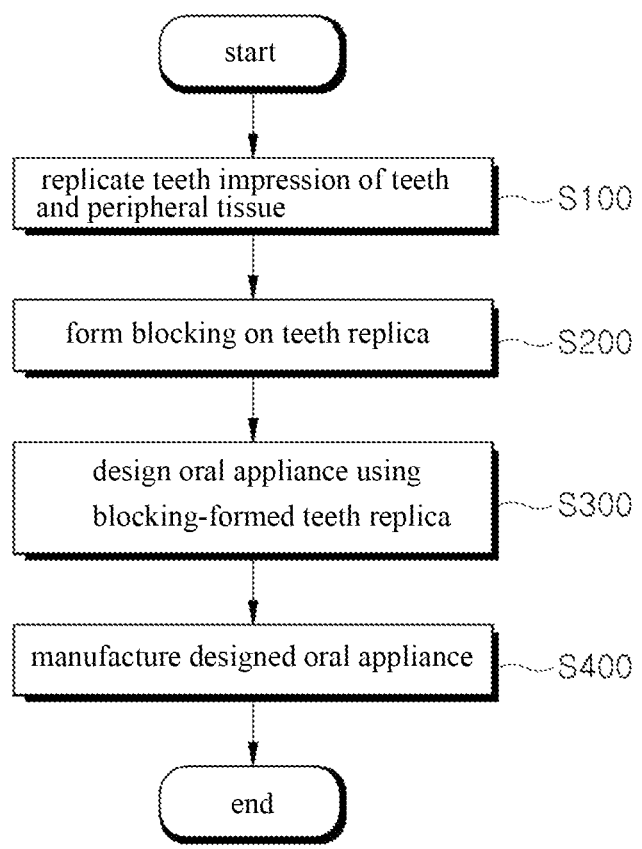
FIG. 7 is a flowchart illustrating a method for manufacturing an oral appliance according to an embodiment of the present invention.

FIG. 7 is a flowchart illustrating a method for manufacturing an oral appliance according to an embodiment of the present invention Referring to FIG. 7, a method for manufacturing an oral appliance of the present invention may include the step s100 of replicating impressions of teeth and peripheral tissues, the step s200 of forming a blocking in the teeth replica, the step s300 of designing an oral appliance using the blocking-formed teeth replica, and the step s400 of creating the oral appliance designed.

The step s100 of replicating the impressions of the teeth and peripheral tissues is a step for preparing a teeth replica that is the same in shape as the teeth of the user who intends to wear the oral appliance 100 of the present invention. The teeth replica which is the same in shape as the user's teeth may be created using plaster molds or a medical device capable of capturing teeth images.

The step s200 of forming a blocking in the teeth replica is a step for forming a blocking on the surface of the teeth replica prepared in the step s100 of replicating the impressions of the teeth and peripheral tissues. At this time, the thickness of the blocking is determined to differ between the incisor part and the molar part. In other words, a blocking margin is set to prevent the anterior teeth from friction against the upper groove or lower groove given a gentle parabolic up-and-down motion of the anterior teeth for the incisor part. For the molar part, a blocking margin is set to allow the molar part to be tightly fastened to the molars.

The step s300 of designing an oral appliance using the blocking-formed teeth replica is a step for creating a design drawing or molds to manufacture the oral appliance of the present invention, with the blocking attached to the teeth replica. The design drawing or molds to manufacture the oral appliance may be created by scanning or capturing in three-dimension (3D) the blocking-attached teeth replica. Or, the molds to manufacture the oral appliance may directly be designed by forming a medical resin on the outside of the blocking-attached teeth replica.

The step s400 of manufacturing an oral appliance as designed is a step for manufacturing an oral appliance based on the drawing or values prepared in the step s300 of designing an oral appliance. Upon using data scanned or captured in 3D, a 3D printer, CAD, or a cam may be used to manufacture an oral appliance. In case of using a medical resin, the medical resin may be formed to be able to be worn in the user's mouth, followed by the process of removing the teeth replica and blocking.

Figure 8:
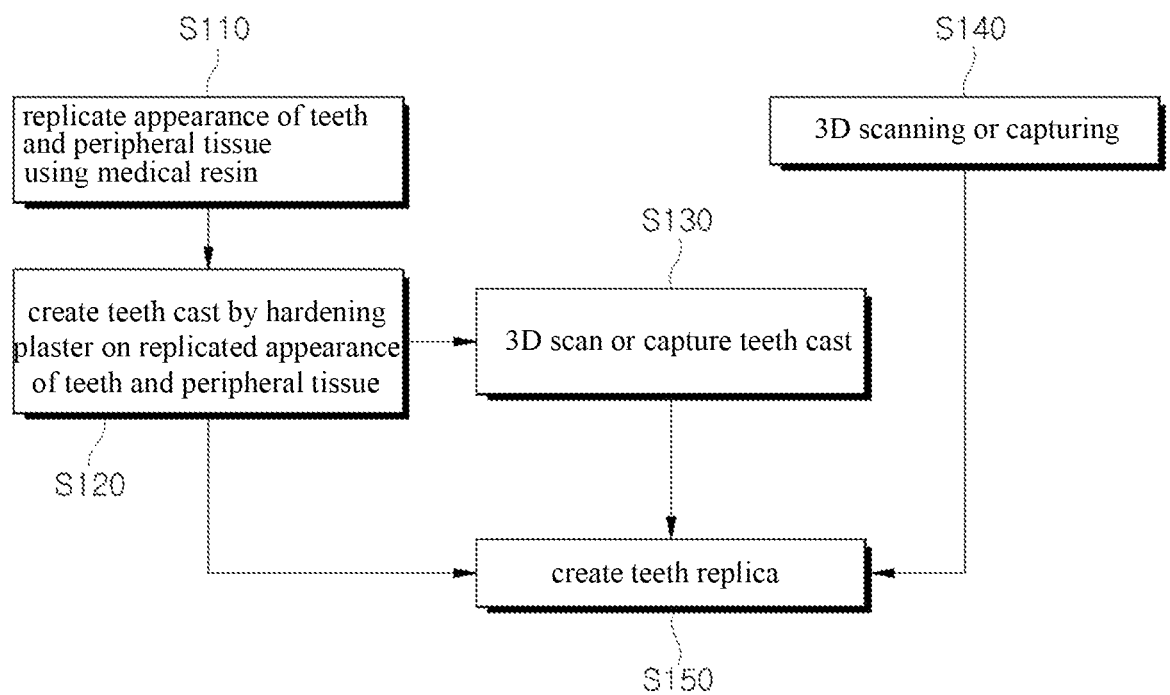
FIG. 8 is a detailed flowchart illustrating a process for replicating a teeth replica in a method for manufacturing an oral appliance according to an embodiment of the present invention.

FIG. 8 is a detailed flowchart illustrating a process for replicating teeth impressions in a method for manufacturing an oral appliance according to an embodiment of the present invention. Referring to FIG. 8, the step s100 of replicating the teeth impressions may be divided into physically preparing a teeth replica or capturing the user's oral condition using a 3D scanning or capturing scheme followed by manufacturing a teeth replica using a 3D printer, CAD, or cam.

To physically prepare the teeth replica, a material, e.g., medical resin, is used to form molds on the user's teeth, replicating the user's teeth appearance (s110). After replicating the user's teeth appearance, a material, e.g., plaster, is hardened into a teeth cast which is the same in shape as the teeth (s120), and the teeth cast may be used as the teeth replica (s150).

In contrast, 3D data for the teeth structure may be obtained via 3D scanning or capturing that reflects the user's teeth structure (s140) in which case a panoramic, cephalometric, or computed tomography scheme for the user's oral condition may be adopted. The 3D data may also be secured by capturing the same teeth structure as the user's teeth structure using plaster (s130). By using the so-obtained 3D data for the user's teeth structure, the user's teeth replica may be created via a 3D printer, CAD, or cam (s150).

Figure 9:
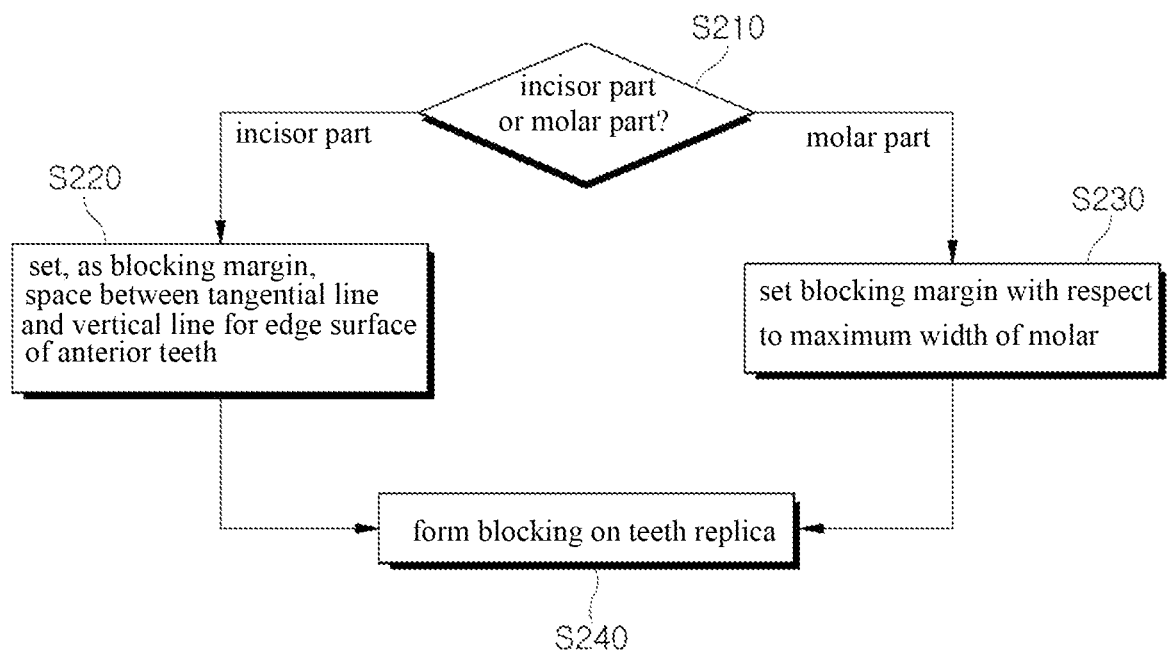
FIG. 9 is a detailed flowchart illustrating forming a blocking on a teeth replica in a method for manufacturing an oral appliance according to an embodiment of the present invention.

FIG. 9 is a detailed flowchart illustrating forming a blocking on a teeth replica in a method for manufacturing an oral appliance according to an embodiment of the present invention. Referring to FIG. 9, whether a blocking is formed on an incisor part or molar part is first determined to form the blocking on a teeth replica (s210).

Where the blocking is formed on the incisor part, it is preferable to leave such an extent of margin as to prevent friction against the inner wall of the upper groove 300 or lower groove 400 while the anterior teeth of the upper jaw or lower jaw are fitted or escaped from the upper groove 300 or lower groove 400 along a gentle parabola. To that end, a blocking margin is set to allow the blocking to be formed within a range of a space between a vertical line and a tangential line with respect to the edge surface of the anterior teeth (s220).

In the case of the molar part, however, since at least one of the upper or lower molars is tightly fastened to the upper groove or lower groove which corresponds to the molars, an additional margin which requires a blocking is set with respect to the left-right maximum width of the molar which is to be fastened (s230). In general, the blocking margin of the molar part would have a value within 2 mm or less from the surface of the molars.

Meanwhile, although an example has been described in which the oral appliance is divided into two parts, i.e., the incisor part and molar part to which different blocking margins are applied, such a case may also be possible as to divide the oral appliance into three or more parts, e.g., by further dividing the incisor part or molar part and setting different blocking margins for the parts.

By wearing an oral appliance according to the present invention as described above, the user may smoothly breathe during sleep thanks to the forward movement of the lower jaw (LJ) while naturally moving the lower jaw (LJ). A fastening force for the oral appliance may be secured by setting a blocking margin in such an extent that the oral appliance may be fastened by a frictional force with respect to the maximum width of the molars for the molar part corresponding to the molars which the oral appliance is fitted over. In contrast, the incisor part for the anterior teeth which move up and down along a gentle parabola is configured to minimize friction between the anterior teeth and the inner wall of the upper groove or lower groove given the trajectory along which the anterior teeth travel, allowing the user to conveniently move his upper jaw and lower jaw while wearing the oral appliance. As a result, the oral appliance of the present invention would not cause pains, malocclusion, or temporomandibular disorder despite a long-term use and may smoothen the air flow through the user's airway (AW), mitigating snoring, sleep apnea, or other symptoms.

Although embodiments of the present invention have been described with reference to the accompanying drawings, it will be appreciated by one of ordinary skill in the art that the present disclosure may be implemented in other various specific forms without changing the essence or technical spirit of the present disclosure. Thus, it should be noted that the above-described embodiments are provided as examples and should not be interpreted as limiting. It should be noted that the scope of the present invention is defined by the appended claims rather than the described description of the embodiments and include all modifications or changes made to the claims or equivalents of the claims.

| [Description of Symbols] | |
|---|---|
| 100: oral appliance body | 300: upper groove |
| 400: lower groove | 500: guide part |
| 600: blocking | |

What is claimed is:

1. A method for manufacturing an oral appliance, the method comprising:
   replicating a teeth impression of teeth and peripheral tissues;
   forming a blocking on the teeth replica, wherein different blocking margins are applied to an incisor part and a molar part;
   designing the oral appliance using the blocking-formed teeth replica; and
   manufacturing the designed oral appliance,
   wherein forming the blocking includes:
   when the blocking is formed on the incisor part, setting a thickness of the blocking using, as a blocking margin, a space between a tangential line and a vertical line for a foremost edge surface of anterior teeth; and attaching the blocking to a surface of the incisor part depending on the blocking margin.

2. The method of claim 1, wherein replicating the teeth impression of the teeth and the peripheral tissues includes:
   replicating an appearance of the teeth and the peripheral tissues using a medical material;
   creating a teeth cast by hardening plaster on the replicated appearance of the teeth and the peripheral tissues; and
   creating the teeth replica using the teeth cast.

3. The method of claim 1, wherein replicating the teeth impression of the teeth and the peripheral tissues includes:
   replicating an appearance of the teeth and the peripheral tissues using a medical material;
   creating a teeth cast by hardening plaster on the replicated appearance;
   obtaining three-dimensional (3D) data by scanning or capturing the teeth cast in 3D; and
   creating the teeth replica using the 3D data.

4. The method of claim 1, wherein replicating the teeth impression of the teeth and the peripheral tissues includes:
   obtaining 3D data for a teeth structure by scanning or capturing a user's mouth in 3D; and
   creating the teeth replica using the 3D data.

5. The method of claim 1, wherein the blocking margin is a distance of 2.5 mm or less away from the edge surface of the anterior teeth.

6. The method of claim 1, wherein forming the blocking includes:
   when the blocking is formed on the molar part, setting a thickness of the blocking using, as a blocking margin, a maximum width of a molar; and
   attaching the blocking to a surface of the molar part depending on the blocking margin.

7. The method of claim 6, wherein the blocking margin is a distance of 2 mm or less away from a side surface of the molar.

8. The method of claim 1, wherein designing the oral appliance includes obtaining 3D data by scanning or capturing the blocking-formed teeth replica in 3D.

9. The method of claim 1, wherein the oral appliance is manufactured by attaching or applying a medical material onto an outside of the blocking-formed teeth replica.

10. The method of claim 1, wherein the oral appliance is manufactured by one or more of methods using a 3D printer, a CAD, and a cam depending on the designed data.

* * * * *